United States Patent [19]

Haar, Jr. et al.

[11] Patent Number: 5,998,492

[45] Date of Patent: Dec. 7, 1999

[54] SUPER-ABSORBING POLYMERIC NETWORKS

[75] Inventors: Joseph P. Haar, Jr., Wheaton; Robert J. Ross, Elmhurst, both of Ill.

[73] Assignee: Donlar Corporation, Bedford Park, Ill.

[21] Appl. No.: 09/178,963

[22] Filed: Oct. 26, 1998

Related U.S. Application Data

[60] Continuation-in-part of application No. 08/819,251, Mar. 17, 1997, Pat. No. 5,847,013, which is a division of application No. 08/305,266, Sep. 13, 1994, Pat. No. 5,612,384.

[51] Int. Cl.⁶ ........................................ C08J 9/28
[52] U.S. Cl. .......................... 521/64; 521/183; 521/184; 528/271; 528/310; 528/328; 528/335; 528/336; 528/363
[58] Field of Search ........................... 521/64, 183, 184; 528/271, 310, 328, 335, 336, 363

[56] References Cited

U.S. PATENT DOCUMENTS

| | | | |
|---|---|---|---|
| 3,846,380 | 11/1974 | Fujimoto et al. | 260/78 |
| 5,057,597 | 10/1991 | Koskan | 528/328 |
| 5,116,513 | 5/1992 | Koskan et al. | 210/698 |
| 5,219,952 | 6/1993 | Koskan et al. | 525/419 |
| 5,221,733 | 6/1993 | Koskan et al. | 530/333 |
| 5,284,936 | 2/1994 | Donachy et al. | 530/350 |
| 5,357,004 | 10/1994 | Carlton et al. | 525/435 |
| 5,391,642 | 2/1995 | Wood | 525/435 |
| 5,461,085 | 10/1995 | Nagatomo et al. | 521/183 |
| 5,508,434 | 4/1996 | Batzel et al. | 548/520 |
| 5,612,384 | 3/1997 | Ross et al | 521/64 |

FOREIGN PATENT DOCUMENTS

| | | |
|---|---|---|
| 92/13566 | 8/1992 | WIPO . |
| 92/17525 | 10/1992 | WIPO . |

OTHER PUBLICATIONS

Neri, P., et al., "Synthesis of α,β–Poly[(2–hydroxyethyl)–D-L–aspartamide], a New Plasma Expander", *Journal of Medicinal Chemistry*, 16, 893–897 (1973).

Fox, S. W., et al., "The Thermal Copolymerization of Amino Acids Common to Protein", *Journal of the American Chemical Society*, 82, 3745–3751 (1960).

*Primary Examiner*—John M. Cooney, Jr.
*Attorney, Agent, or Firm*—Olson & Hierl, Ltd.

[57] ABSTRACT

Disclosed are methods of producing super-absorbing polymeric networks of polyaspartates from crosslinked polysuccinimide. In one preferred aspect, polysuccinimide is first reacted with an organic crosslinking agent, preferably an organic base containing at least two primary amine groups, to form a gelled crosslinked polysuccinimide. The gelled crosslinked polysuccinimide is then base hydrolyzed to a gelled polymeric network of polyaspartate and deswollen with at least one liquid alcohol to a polymeric network of polyaspartate which demonstrates super-absorbing capability in water and in electrolyte solution. Super-absorbing polymeric networks of polyaspartates can also be produced in a single reaction vessel by sequentially crosslinking a polysuccinimide with an organic crosslinking agent in an aqueous reaction medium, optionally containing a mineral acid, and then hydrolyzing the crosslinked polysuccinimide to produce a polymeric network of polyaspartate.

19 Claims, 1 Drawing Sheet

FIG. 1

SUPER-ABSORBING POLYMERIC NETWORKS

CROSS-REFERENCE TO RELATED APPLICATION

This application is a continuation-in-part of U.S. Ser. No. 08/819,251, filed on Mar. 17, 1997, now U.S. Pat. No. 5,847,013, which is a division of U.S. Ser. No. 08/305,266, filed on Sep. 13, 1994, now U.S. Pat. No. 5,612,384.

FIELD OF THE INVENTION

The present invention relates to the field of crosslinked polymers. More particularly, the invention relates to new polymeric networks capable of absorbing large quantities of water, aqueous solutions or polar organic solvents, and methods for preparing such super-absorbing polymeric networks.

BACKGROUND OF THE INVENTION

The term "water-swellable polymeric networks" as used herein refers to highly crosslinked polymers which have a propensity to swell or gel in the presence of water. Water-swellable polymeric networks have found wide use in a variety of applications. See, for example, Odian, G., *Principles of Polymerization*, 3rd Edition, published by Wiley-Interscience, New York, 1991 and Glass, J. E., Ed. "Polymers in Aqueous Media Performance Through Association," *Advances in Chemistry Series* 223, published by the American Chemical Society, Washington, D. C., 1989).

Water-swellable polymeric networks which are well known in the polymer arts include, but are not limited to, carboxymethylcellulose, crosslinked polyacrylates, graft copolymer hydrolysis products of starch-acrylonitrile, polyvinyl alcohol resins, polyethylene oxide resins and polyacrylonitrile resins.

Several problems are associated with such polymeric networks. First, their water absorbency properties are greatly reduced in the presence of salts, such as sodium chloride, which are often present in the environments where such polymeric materials are used. Second, most of these polymeric materials are not readily biodegradable and thus contribute to the overall chemical burden on the environment when they are released into effluent streams.

Some crosslinked polypeptides containing a high percentage of anionic amino acids, such as aspartic acid or glutamic acid, are useful as super-absorbing materials. Some of these are disclosed in International Patent Publication WO 92/17525 and in U.S. Pat. No. 5,284,936 to Donachy, et al. Such materials have improved saline absorbency and are biodegradable. However, they require amino acids as starting materials and these are relatively expensive.

Koskan, et al. in U.S. Pat. Nos. 5,057,597, 5,116,513, 5,219,952 and 5,221,733 describe inexpensive methods for the manufacture of polysuccinimide and polyaspartic acid. The chemical modification of polysuccinimide to produce useful polyaspartates is well known. For example, Neri, et al., in the article, "Synthesis of alpha, beta-Poly[(2-hydroxyethyl)-D,L-aspartamide], a New Plasma Expander," *Journal of Medicinal Chemistry*, Vol. 16, pp 893–897, (1973) describe the modification of polysuccinimide with ethanolamine.

Fujimoto et al. in U.S. Pat. No. 3,846,380 describe the formation of modified polypeptides having hydrophobic and hydrophilic substituents as side chains obtained by reacting polysuccinimide with at least one primary or secondary aliphatic amine and hydrolyzing the resulting polyamide derivative with alkali to produce polypeptides that are useful as surface active agents.

U.S. Pat. No. 5,461,085 to Nagatomo describes a method of producing alkali-unstable water-insoluble super-absorbing polymers by partially crosslinking polysuccinimide with a diamine compound in an organic solvent or aqueous solution and hydrolyzing the imide ring of the reaction product with aqueous alkali metal hydroxide under controlled pH conditions to avoid unfavorably hydrolyzing the amide linkage in the main chain. However, the Nagatomo method requires careful process controls in multiple steps which adds costs to the process.

There is an ongoing need and desire, therefore, for an economical method of substantially rapidly producing biodegradable, polyaspartate-based super-absorbing polymeric networks with improved electrolyte tolerance.

SUMMARY OF THE INVENTION

The present invention provides an economical, improved method of producing biodegradable, super-absorbing polymeric networks by chemical modification of polysuccinimide. The term "polymeric networks" as used herein refers to random copolymers of crosslinked polyaspartate which can swell or gel in water or electrolyte solutions. The term "super-absorbing polymeric networks" and grammatical variations thereof as used herein refer to polymeric networks of crosslinked polyaspartates which can absorb from at least 3 times to more than 260 times their weight in water and from at least 2 times to more than 40 times their weight of an electrolyte solution, such as aqueous 1% sodium chloride (saline solution) or urine.

The term "polyaspartate" and grammatical variations thereof as used herein, includes polyaspartic acid as well as salts of polyaspartic acid. Polyaspartates suitable for preparing super-absorbing polymeric networks of the present invention can be synthesized by several methods, all of which initially involve the reaction of polysuccinimide with an organic crosslinking agent.

One preferred method comprises reacting, in a reaction medium, a polysuccinimide with an organic crosslinking agent containing at least two primary amine groups. The crosslinking agent is present in an amount sufficient to form a gelled crosslinked polysuccinimide product. The gelled crosslinked polysuccinimide is subsequently base hydrolyzed to a gelled polymeric network of polyaspartate, and deswelled at a pH in the range of about 6 to about 12 by contacting with at least one liquid, monohydric, aliphatic alcohol. The super-absorbing polymeric network of polyaspartate (SPNP) produced can be recovered in a substantially dry form.

Advantageously, super-absorbing polymeric networks of this invention can be prepared in a single reaction vessel in alternative preferred method aspects.

In one method aspect, the gelled crosslinked polysuccinimide can be prepared in a liquid medium selected from water, water-miscible, polar aprotic solvent and mixtures thereof.

In another method aspect, the gelled polymeric network of polyaspartate can be isolated from the reaction medium prior to deswelling, by sequentially acidifying to a pH value in the range of about 1 to about 5, washing with water, and suspending in water made basic by adjusting the pH to a value in the range of about 6 to about 12, preferably in the range of about 9 to about 10.

An alternative preferred method comprises reacting polysuccinimide with an organic base containing at least two primary amine groups in an aqueous reaction medium which optionally contains a mineral acid, and then hydrolyzing the obtained crosslinked polysuccinimide to produce a super-absorbing polymeric network of polyaspartate.

If desired, polysuccinimide may first be reacted with the organic base in a polar aprotic solvent to form crosslinked polysuccinimide which then can be collected for subsequent hydrolysis to produce a super-absorbing polymeric network of polyaspartate.

In another method aspect, polysuccinimide is crosslinked in an aqueous reaction medium, preferably containing a mineral acid, and an effective crosslinking amount of a latent organic crosslinking agent from which free organic crosslinking agent can be released by base neutralization to produce crosslinked polysuccinimide. The crosslinked polysuccinimide product then can be further base hydrolyzed to produce a polymeric network of polyaspartate.

The polymeric networks of the present invention are useful in a wide variety of applications, where liquid absorption, viscosity modification, chemical sequestration or dehydration is required or desired. For example, applications include the use of polymeric networks as super absorbents for body fluids in diapers, incontinence products and sanitary napkins; as humectants in agricultural products; as sludge coagulants in water treatment; as viscosity modifiers in the petroleum industry; as dehydrating agents; as chemical absorbents (e.g. for clean-up of chemical spills); for controlled release of chemicals; for microencapsulation; as thickening agents; as media for electrophoresis and chromatography (e.g. for gel permeation chromatography, capillary electrophoresis, etc.); in soft contact lens manufacture; and as moisturizing components in consumer products, such as personal care products or the like.

DETAILED DESCRIPTION OF THE INVENTION

The term "polysuccinimide" as used herein defines a homopolymer having the structural formula (I), wherein n is greater than about 5.

(I)

Polysuccinimides suitable for preparing super-absorbing polymeric networks of the present invention can be synthesized by any of several methods known in the art.

Figure 1:
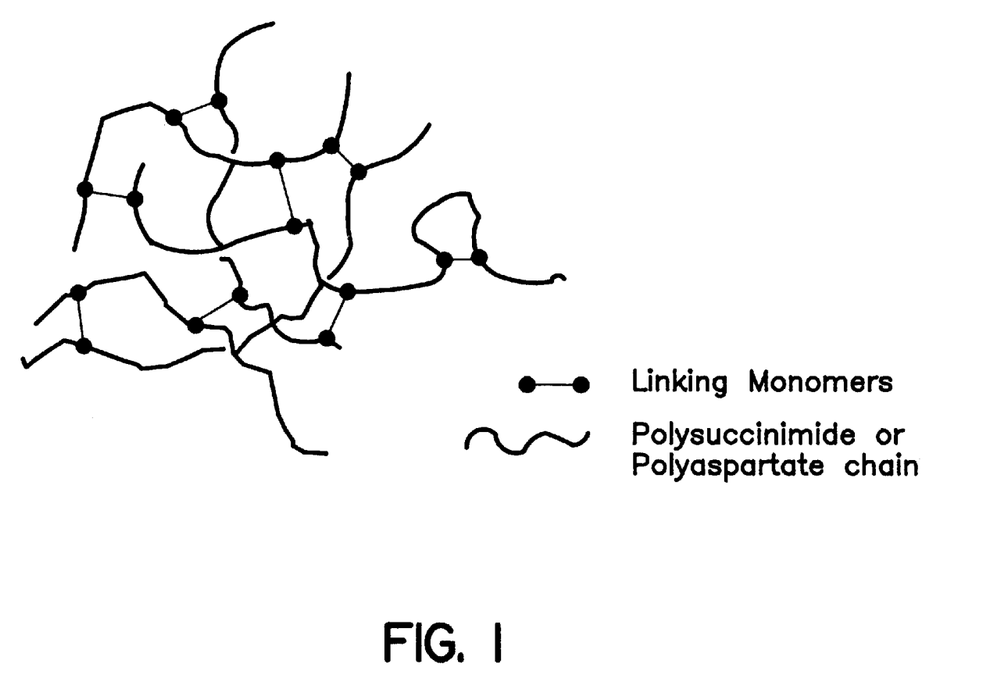
FIG. 1 is a graphic depiction of a super-absorbing polymeric network embodying the principles of this invention comprised of linking monomer units, crosslinked polysuccinimide and crosslinked polyaspartate chains.

As shown in FIG. 1, the super-absorbing polymeric networks of this invention are random copolymers structurally comprised of monomer units of succinimide (structural formula S), alpha-aspartate (structural formula A), beta-aspartate (structural formula B) and crosslinking dimeric aspartamides (structural formula having any one of the following three structural formulas, $L^1$, $L^2$, and $L^3$). For convenience, these will be referred to generally as structural formula (L).

Succinimdie Monomer (S)

Alpha-aspartate Monomer (A)

Beta-aspartate Monomer (B)

In the structural units, A and B, M can be hydrogen, an alkali metal cation such as $Na^+$, $K^+$ or $Li^+$, ammonium, or quaternary ammonium.

Crosslinking Monomer ($L^1$)

Crosslinking Monomer ($L^2$)

Crosslinking Monomer ($L^3$)

In the structural L units, $L^1$, $L^2$ and $L^3$, R is a divalent organic linking group derived from the organic crosslinking agent. The organic crosslinking agent preferably is an organic base containing at least two primary amine groups capable of reacting with a succinimide monomer unit to form a crosslink thereof. For convenience, reference to "L units" includes any one of the foregoing monomeric crosslinking L structural units without limitation.

The term "crosslinked polyaspartate" or "crosslinked polyaspartic acid" as used herein refers to polymeric networks which are random copolymers structurally comprised primary of A, B and L units and are water-swellable and electrolyte solution swellable. Preferably, crosslinked polyaspartates contain no S units or relatively small amount thereof, e.g., less than about 20% S units. The term "crosslinked polysuccinimide" as used herein refers to random copolymers comprised primarily of S and L units. Crosslinked Polysuccinimides preferably contain no A and B units or relatively small proportions of A and B units so that the combined amount of A+B units is less than about 20%.

For convenience, the methods of this invention will be illustrated and discussed using diamine crosslinking agents. A "diamine crosslinking agent" refers herein to an organic base having at least two primary amine groups available for reaction with the succinimide monomer units of polysuccinimide to form a crosslink.

Useful polysuccinimide for the methods of this invention may be synthesized by any method, for example by thermal polymerization of aspartic acid, by thermal polymerization of aspartic acid in the presence of phosphoric acid or polyphosphoric acid, by thermal polymerization of maleic acid and ammonia, or any other suitable method. Preferably, the weight average molecular weight ($M_W$) of polysuccinimide is in a range of about 500 to greater than about 150,000, more preferably in a range of about 1500 to about 80,000 and most preferably in a range of about 5,000 and about 50,000.

The amount of the diamine crosslinking agent is preferably in a range of about 0.001 moles to about 5 moles per kilogram of succinimide. Using a formula weight (FW) of 97 for polysuccinimide (the formula weight of a succinimide monomer unit), the amount of organic diamine component can also be expressed as moles of diamine per mole of succinimide monomer units×100%, hereafter referred to as "mole %". On this basis, the amount of diamine crosslinking agent can be in a range of about 0.1 to about 50 mole %.

The preferred mole % of diamine is dependent upon the weight average molecular weight ($M_W$) of the polysuccinimide starting material. For polysuccinimides of $M_W$ in the range of about 500 and about 4000, the preferred amount of diamine crosslinking agent is about 10 to about 30 mole %. For polysuccinimides of $M_W$ between about 4,000 to about 10,000, the preferred amount of diamine crosslinking agent is about 1 to about 20 mole %. For polysuccinimides of $M_W$ greater than about 10,000 the preferred amount of available diamine crosslinking agent is in the range of about 0.5 to about 15 mole %.

The crosslinking can occur between adjacent polymer chains or within the same polymer chain or both. Multiple crosslinks can also be incorporated into the polymer chains.

Compounds useful as diamine crosslinking agents in practicing the methods of the present invention include, but are not limited to, aliphatic diamines, such as ethylenediamine (EDA), 1,3-bis(aminomethyl)cyclohexane (1,3-BAC), and hexamethylene diamine (HMDA); arylaliphatic diamines, such as meta-xylylene diamine (MXDA); polyether diamines, such as polyoxyalkylenediamines and amine terminated block copolymers of polyoxyalkylene/polyalkylene glycols, sold in varying approximate molecular weights in the range of about 280 to about 2,000 under the trademark JEFFAMINE™ by Huntsman Chemical Company; and diamino acid or amino acid derived diamines such as lysine, lysine methyl ester, cystamine, cystine, cystine dimethyl ester, or the like.

According to the supplier, the JEFFAMINE™ ED series products are amine terminated polypropylene glycols having an average of about 2 to about 68 propylene oxide units, the JEFFAMINE™ ED series of products are amine terminated polyethylene/polypropylene glycols, having a predominantly polyethylene oxide backbone. Other useful polyether amines are triethyleneglycol diamine (JEFFAMINE™ EDR-148, or Huntsman XTJ-504) and tetraethyleneglycol diamine (JEFFAMINE™ EDR-192).

Also useful are amine terminated polyalkyleneimines, such as amine terminated polyethyleneimines including, for example, triamines and pentamines, such as diethylenetriamine (DETA) and tetraethylenepentamine (TEPA).

Additionally, triamino, tetraamino and polyamino organic compounds can also be used as organic crosslinking agents to form new polymeric networks of the present invention as long as the functional amino groups needed for crosslinking are present. The use of such amino compounds can further lead to incorporation of linking monomer units such as the following $L^4$ and $L^5$ structural formulas, where $R^2$ is a trivalent or tetravalent organic radical linking group derived from the organic crosslinking agent.

Trivalent Crosslinking Monomer ($L^4$)

-continued

Trivalent Crosslinking
Monomer (L⁵)

Examples of triamino, tetraamino and polyamino compounds useful as organic crosslinking agents in the present invention include, but are not limited to tris(2-aminoethyl) amine (TAEA), polyamine compounds sold under the trademark STARBURST™ Dendrimers by Dendritech, Inc., the propylene oxide based triamine series sold in various approximate molecular weights ranging from about 440 to about 5,000 under the trademark JEFFAMINE™ by Huntsman Chemical Company, and polyvinylamine polymers.

Preferably, super-absorbing polymeric networks of the present invention swell or gel in the presence of water to at least about 3 times to over 250 times, preferably about 25 times to over 260 times their dry weight, and in the presence of electrolyte solution, such as aqueous 1% sodium chloride (saline) or urine, to at least about 2 times to over 30 times, preferably about 5 times to over 40 times, their dry weight.

In one preferred method aspect, polymeric networks of crosslinked polyaspartates may be produced by first crosslinking polysuccinimide with an organic crosslinking agent in the presence of a polar aprotic solvent. The reaction may be carried out by heating the reaction medium to a temperature in the range of about 25° C. to about 160° C., preferably in the range of about 25° C. to about 80° C., and maintaining the temperature until crosslinked polysuccinimide product forms. Preferably the crosslinked polysuccinimide product is in the form of a gel. The crosslinked polysuccinimide product then can be hydrolyzed to a polymeric network comprising polyaspartate. The product polymeric network may be in the form of a gel or solid, preferably a gel, which then can be substantially dried for use as a super-absorbing polymeric network of polyaspartate (SPNP).

Useful polar aprotic solvents include dimethylsulfoxide, dimethylformamide, dimethylacetamide and sulfolane but are not limited thereto. Preferably, the aprotic solvent is at least water-miscible. The crosslinked polysuccinimide product is preferably isolated by admixing the reaction medium with a polar solvent, preferably water or an alcohol, in which the polar aprotic solvent is soluble but in which the crosslinked polysuccinimide product is not soluble to precipitate the polymer. Preferably, the reaction medium is cooled to about ambient room temperature prior to isolating the crosslinked polysuccinimide product.

Base hydrolysis can be achieved by treating the crosslinked polysuccinimide with alkali metal hydroxide, preferably in water. Surprisingly, isolating the resultant gelled polymeric network of polyaspartate with water and deswelling the gelled product with at least one liquid, monohydric alcohol greatly improves the processing of the super-absorbing polymeric network of crosslinked polyaspartate. Preferred liquid, monohydric aliphatic alcohols include ethanol, methanol, propanol, isopropanol, butanol and the like and mixtures thereof.

In alternative method aspects, a super-absorbing polymeric network of polyaspartate may be produced in an aqueous reaction medium using a single reaction vessel.

In a preferred method, an aqueous solution of organic crosslinking agent is first substantially neutralized with a sufficient amount of a relatively strong mineral acid, preferably hydrochloric acid, phosphoric acid, sulfuric acid, nitric acid or the like, to form a water-soluble acid salt thereof. Next, polysuccinimide is admixed therein to form a slurry with the salt solution. The polysuccinimide is subsequently crosslinked by adding sufficient aqueous sodium hydroxide to release a crosslinking amount of free organic crosslinking agent in the reaction medium to produce crosslinked polysuccinimide. The crosslinked polysuccinimide product is then further base hydrolyzed to a super-absorbing polymeric network of polyaspartate.

In another method aspect, polysuccinimide can be slurried in water and the slurry admixed with an effective crosslinking amount of organic crosslinking agent. The crosslinked polysuccinimide product then can be treated with aqueous alkali metal hydroxide to produce a super-absorbing polymeric network of polyaspartate.

In a particularly preferred method, polysuccinimide may be slurried in water in an amount of about 1 to about 10 times the weight of polysuccinimide and mineral acid may be added in an amount of about 0.1% to 100% by weight based on the polysuccinimide weight. At least one diamine crosslinking agent is then added to the mixture (in a quantity from about 0.1 mole % to about 50 mole %, based on succinimide units in the polysuccinimde) followed by a sufficient quantity of alkali metal hydroxide to release an effective crosslinking amount of free organic crosslinking agent to simultaneously induce crosslinking of the polysuccinimide and hydrolyze remaining succinimide units in the polymer to polyaspartate units. Preferably about 100 mole % to about 400 mole % of alkali metal hydroxide, based on succinimide units in the polysuccinimde is employed. Such a process produces crosslinked polyaspartate super-absorbing polymeric networks of relatively high water absorbency.

The alkali metal hydroxide is preferably added over a time period in the range of about 5 minutes to about 5 hours. The alkali metal hydroxide may be added in the form of a solid or as an aqueous solution. Additionally, the amount of diamine crosslinking agent can be added either all at once, in incremental, dropwise portions, continuously concurrent with or alternating with the addition of alkali metal hydroxide. The use of mineral acids in the aqueous medium for crosslinking of polysuccinimide is believed to provide a buffering effect that increases the efficiency of the reaction of diamine with succinimide units in the polymer in forming crosslinking units.

A mixture of polysuccinimide, mineral acid and diamine crosslinking agent useful in the present invention may alternatively be obtained by:

a) mixing aspartic acid, mineral acid and diamine crosslinking agent in water to form a reaction medium; and b) heating the resulting reaction medium to a temperature above about 160° C. for a period of time sufficient to polymerize the aspartic acid to polysuccinimide. The crosslinked polysuccinimide product formed in the mixture obtained in this manner then can be treated with aqueous base to a super-absorbing polymeric network of polyaspartate.

The super-absorbing polymeric networks of polyaspartate of the present invention, hereafter for convenience referred to as SNPN, may be recovered by filtering and drying to remove water or solvent residue. Optionally, the SPNP may be washed with water, alcohol, or a mixture of water and alcohol to remove dissolved salts and soluble polymeric materials prior to drying. SPNP may also optionally be deswelled by treatment with liquid, monohydric aliphatic alcohol or by acidification with mineral acid to facilitate the washing process. When acid is used as a deswelling agent, the SPNP gel must be re-neutralized with alkali metal hydroxide or aqueous ammonia to achieve a pH preferably in the range of about 6 to about 12 prior to drying.

The following examples illustrate the preparation of embodiments of super-absorbing polymeric networks of polyaspartates from crosslinked polysuccinimide by the methods discussed. The examples and methods presented are illustrations of preferred embodiments and are not intended as limitations.

Preparation of Crosslinked Polysuccinimide (Method A)

To illustrate the methods of this invention, crosslinked polysuccinimide described in examples 1–17 were synthesized by the following general method referred to as Method A.

Polysuccinimide of a given $M_W$ was dissolved in polar aprotic solvent employing about 10 mL solvent/gram, for example, dimethylsulfoxide (DMSO) or dimethylformamide (DMF), as indicated below. A selected mole % of diamine crosslinking agent was then added. The reaction medium can be heated to accelerate the crosslinking reaction. Preferably, the temperature of the reaction medium was in the range of about 25° C. to about 160° C., more preferably in the range of about 45° C. to about 50° C. The resulting crosslinked polysuccinimide product was generally in the form of a gel or a solid precipitate. This product was then isolated by pouring the reaction medium into a solvent, such as water or an alcohol, in which the polar aprotic solvent is soluble, but in which the polymer is not. This produced a solid or precipitate, which can be isolated by filtration and dried.

EXAMPLE 1
Synthesis of Crosslinked Polysuccinimide by Method A

As shown in Table 1, polysuccinimide having a $M_W$ of about 5100 (about 9.78 g, 100 mmole of succinimide units) was dissolved in DMSO solvent (about 100 mL) at a temperature of about 40° C. Ethylenediamine (EDA) (about 1 g, 10 mmole) was then added with stirring over a period of about 5 minutes at a temperature of from about 45° C. to about 50° C. A gelatinous reaction medium of crosslinked polysuccinimide formed after a few minutes.

Next, the gelatinous reaction medium was heated at a temperature of about 50° C. for about an additional 2 hours to ensure complete reaction. The gelatinous reaction medium was then cooled to about ambient temperature. The cooled reaction medium was poured into about 600 mL of methanol with stirring. A pinkish-tan colored precipitate was produced. The product was collected by filtration and substantially dried at about 70° C. The yield was about 10.2 grams.

EXAMPLES 2–17
Synthesis of Crosslinked Polysuccinimides

Other examples of crosslinked polysuccinimides were successfully made by following the method of Example 1, except that the diamine crosslinking agent, mole % amount thereof, polysuccinimide of given $M_W$ and solvent employed were as listed in Table 1.

TABLE 1

CROSSLINKED POLYSUCCINIMIDES

| Example | Diamine[1] | Polysuccinimide Mol. Wt. ($M_w$) | Mole % Diamine | Solvent[2] |
|---|---|---|---|---|
| 1 | EDA | 5100 | 10 | DMSO |
| 2 | EDA | 5100 | 5 | DMSO |
| 3 | EDA | 5100 | 15 | DMSO |
| 4 | MXDA | 5100 | 7 | DMSO |
| 5 | EDA | 5100 | 10 | DMF |
| 6 | MXDA | 5100 | 11 | DMSO |
| 7 | 1,3-BAC | 5100 | 7 | DMF |
| 8 | 1,3-BAC | 5100 | 11 | DMF |
| 9 | EDR-148 | 5100 | 10 | DMF |
| 10 | EDR-148 | 5100 | 15 | DMF |
| 11 | EDR-48 | 5100 | 20 | DMF |
| 12 | MXDA | 5100 | 15 | DMF |
| 13 | DETA | 5100 | 10 | DMF |
| 14 | TEAE | 5100 | 10 | DMF |
| 15 | EDA | 1500 | 20 | DMF |
| 16 | EDR-148 | 30,000 | 13 | DMSO |
| 17 | EDA | 30,000 | 4 | DMF |

Notes To TABLE 1
[1]Diamine = diamine crosslinking agent
MXDA = meta-xylylenediamine
EDA = ethylenediamine
1,3-BAC = 1,3- bis(aminomethyl)cyclohexane
EDR-148 = triethyleneglycol diamine, approximate molecular weight 148 (JEFFAMINE ™EDR-148, Texaco Chemical Company, now Huntsman Chemical Company)
DETA = diethylenetriamine
TAEA = tris(2-aminoethyl)amine
[2]DMSO = dimethylsulfoxide
DMF = dimethylformamide Preparation of Polymeric Networks of Crosslinked Polyaspartate (Method B)

In Examples 18–23 and 25–29, polymeric networks of crosslinked polyaspartate Examples were synthesized by Method B, described generally as follows.

A crosslinked polysuccinimide was first prepared by the general Method A discussed above. The crosslinked polysuccinimide was then suspended in a sufficient quantity of aqueous sodium hydroxide solution to theoretically completely hydrolyze the polysuccinimide and any remaining succinimide units in the polymer to produce an aqueous gel of crosslinked polyaspartate. The pH of the resulting aqueous polymeric network gel was then adjusted to whatever pH value was desired.

The gel can be substantially dried to a solid at this point, or alternatively, it can be diluted with excess water and washed or dialyzed before the drying step.

EXAMPLE 18
Synthesis of a Polymeric Network of Crosslinked Polyaspartate by Method B A polymeric network of polyaspartate, as shown in Table 2, was prepared from polysuccinimide having a $M_W$ of about 5100 (30 mmole succinimide units) crosslinked by the procedure of Method A with 15 mole % MXDA. The crosslinked polysuccinimide (about 6 g) was admixed with about 30 mL aqueous 1N sodium hydroxide (30 mmole) to a slurry of crosslinked polysuccinimide. A gel reaction medium formed in about 1 minute. Next, water (about 50 mL) was added to make the gel reaction medium stirrable.

The gel reaction medium was heated with stirring at about 50° C. for about 4 hours. The initial pH was 12.6. After about 4 hours, the pH was about 10.8. Next, the gel reaction medium was allowed to stand at ambient room temperature for about 20 hours. The pH was then adjusted to about 9.5 with about 4 mL of 1N HCl. A polymeric network gel was produced, which was allowed to settle. The supernatant liquid was decanted off and the gel was then substantially dried at about 50° C. for about 24 hours. A tan solid was produced. The yield was about 5.9 grams.

EXAMPLES 19–23 AND 25–29
Additional Syntheses

Other polymeric networks of polyaspartates were successfully synthesized by Method B by following the procedure of Example 18 except that the polysuccinimide, diamine crosslinking agent, mole % amounts and pH values employed were as listed in Table 2.

TABLE 2

CROSSLINKED POLYASPARTATES

| Example | Diamine[1] | Polysuccinimide Mol. Wt. ($M_w$) | Mole % Diamine | pH | Method |
|---|---|---|---|---|---|
| 18 | MXDA | 5100 | 15 | 9.5 | B |
| 19 | EDA | 5100 | 10 | 4 | B |
| 20 | EDA | 5100 | 10 | 3.8 | B |
| 21 | EDA | 5100 | 15 | 4 | B |
| 22 | EDA | 5100 | 10 | 9.5 | B |
| 23 | EDA | 5100 | 15 | 9.3 | B |
| 24 | HMDA | 5000 | 15 | 10 | D |
| 25 | 1,3-BAC | 5100 | 11 | 9.5 | B |
| 26 | EDR-148 | 5100 | 15 | 9.7 | B |
| 27 | EDR-148 | 5100 | 20 | 9.5 | B |
| 28 | DETA | 5100 | 10 | 9.5 | B |
| 29 | TAEA | 5100 | 10 | 9.5 | B |
| 30 | EDA | 30000 | 5 | 8.5 | C |
| 31 | EDA | 1500 | 20 | 9.5 | C |
| 32 | EDA | 30000 | 4 | 9.5 | C |
| 33 | EDR-148 | 30000 | 13 | 9.5 | C |
| 34 | EDR-148 | 5000 | 30 | 10 | D |
| 35 | HMDA | 5000 | 7 | 10 | D |
| 36 | HMDA | 5000 | 10 | 10 | D |

Notes to TABLE 2
[1]Diamine = diamine crosslinking agent (See identifying note 1 to TABLE 1).
HMDA = hexamethylenediamine Preparation of Polymeric Networks of Polyaspartate (Method C)

Examples 30–33 illustrate the preparation of polymeric networks of polyaspartate by an alternative method embodiment referred to as Method C. First, polysuccinimide of a given $M_W$ was dissolved in a polar aprotic solvent and a diamine crosslinking agent was added to form crosslinked polysuccinimide generally as described in Method A. The mixture can be heated to ensure complete reaction.

When a gel or solid suspension was produced, it was then diluted with a sufficient quantity of aqueous sodium hydroxide solution to completely hydrolyze the crosslinked polysuccinimide and any remaining succinimide monomer units of the polymer. After completion of the hydrolysis to a polymeric network of polyaspartate, the pH can be adjusted to any value desired.

The resulting polymeric network gel of polyaspartate was then separated from the supernatant fluid by decanting or centrifuging, to remove substantially most of the polar aprotic solvent. The gel was then washed or dialyzed with water to remove any remaining solvent. This produced a water-swollen polymeric network gel.

The water-swelled polymeric network gel was then substantially dried to a solid.

EXAMPLE 30
Synthesis of Polymeric Networks of Polyaspartate by Method C

As shown on Table 2, a polymeric network of polyaspartate was prepared from a crosslinked polysuccinimide prepared generally by Method A as follows. Polysuccinimide was crosslinked by adding ethylenediamine (EDA) (0.25 g, 2.5 mmole) over a period of about 3 minutes to a solution of polysuccinimide of $M_W$ of about 30,000 (about 5 g, about 50 mmole succinimide units) in about 50 mL of DMF solvent at a temperature range of about 45° C. to about 50° C. Within minutes, a substantially clear, firm gel was produced. This gel product was allowed to stand at about 50° C. for about one hour and then cooled to about ambient room temperature. The cooled gel product was allowed to stand at room temperature for about an additional 2 hours.

Next, a polymeric network of polyaspartate was prepared as follows. The gel product was cut up into fine shards and suspended, with stirring, in 1N sodium hydroxide solution (42 mL, 42 mmole) at about 45° C. to about 50° C. Initially, the pH was about 12.9. After about 3 hours, the pH had dropped to about 8.5. A gelatinous solid was produced. The supernatant liquid was then poured off and the gelatinous solid was diluted with about 180 mL of water. A polymeric network gel formed and considerable water swelling of the gel was observed. Excess water was then removed from the water-swollen gel by filtering through a 200 mesh wire sieve.

The filtered water-swollen gel was then diluted with about 100 mL of water, again filtered and the resulting water-swollen polymeric network gel collected. The weight of the water-swollen polymeric network gel was determined to be about 156 grams.

The water-swollen polymeric network gel was then dried at about 70° C. for about 20 hours to afford about 6.85 grams of an off white solid. On the basis of this yield, the water content of the water-swollen polymeric network gel represented about 23 times the weight of the dry polymeric network.

EXAMPLES 31–33
Preparation of Polymeric Networks of Polyaspartate by Method C Other polymeric networks of polyaspartates were successfully synthesized by Method C by following the procedure of Example 30 except that the polysuccinimide, diamine crosslinking agent, mole % amounts and pH values employed were as listed in Table 2.

Preparation of Polymeric Networks of Polyaspartate (Method D)

Examples 24 and 34–36 illustrate the preparation of polymeric networks of polyaspartate by another alternative method embodiment referred to as Method D. First, an aqueous salt solution of organic diamine crosslinking agent was prepared by adding the organic diamine crosslinking agent to water and neutralizing it with hydrochloric acid to form the hydrochloride salt thereof. Polysuccinimide of a selected $M_W$ was then added to form a slurry. Aqueous sodium hydroxide was then added in an amount calculated to neutralize the diamine hydrochloride and generate a crosslinking amount of the free diamine crosslinking agent to react with the polysuccinimide and form crosslinked polysuccinimide.

Next, additional aqueous sodium hydroxide was added in an amount sufficient to hydrolyze the crosslinked polysuccinimide and any remaining succinimide monomer units in the polymer. A polymeric network gel was produced. The polymeric network gel then can be collected and substantially dried.

A variation of this method can be practiced by adding the free diamine crosslinking agent to an aqueous slurry of polysuccinimide, followed by addition of the aqueous sodium hydroxide solution as described above.

EXAMPLE 34

Synthesis of Polymeric Networks of Polyaspartate by Method D

Triethyleneglycol diamine (EDR-148) (about 100 g, 0.67 mole) was acidified with 6N HCl solution to a final pH of about 1.7. The final total weight of the solution was about 305.53 g. Polysuccinimide (about 20 g, 200 mmole of succinimide units, $M_W$ about 5000) and water (about 10 mL) were combined with about 28.84 g (60 mmole) of the neutralized diamine and the mixture was stirred vigorously to form a slurry. Aqueous sodium hydroxide (about 50%) solution was added dropwise at a rate of about 1 mL per min until gel formation occurred (approximately 15 min.). The gel was dried at about 70° C. for about 48 hours and then ground to a powder. The yield was about 26 g.

EXAMPLES 35–36

Syntheses of Polymeric Networks of Polyaspartates by Method D

Other polymeric networks of polyaspartates were successfully synthesized by following the method of Example 34 except that the polysuccinimide, amine crosslinking agent and mole % of amine crosslinking agent employed were as listed in Table 2.

EXAMPLE 37

Super-absorbing Polymeric Networks of Polyaspartates

The super-absorbing characteristics of each of the polymeric networks of crosslinked polyaspartate of Examples 18–36 was demonstrated by the values obtained in the following protocol employing either deionized water or aqueous 1% sodium chloride (saline solution).

Approximately 100 milligrams (mg) of polymeric network of polyaspartate was added into a pre-weighed test tube. An amount of either deionized water or saline solution was added in sufficient excess to the contents of the tube to swell the polymeric network and provide supernatant liquid. The tube was then allowed to stand undisturbed for about 25 minutes, at the end of which time, the tube was centrifuged at about 1500 rpm for about 5 minutes. The supernatant liquid was then removed by pipette.

The tube with its contents was then weighed and the amount of liquid that had been absorbed by the polymeric network was determined. Water absorbency or saline absorbency was expressed as the ratio of the weight of the water swollen or saline swollen polymeric network gel divided by its weight when dry. Each evaluation was made in triplicate and an average value calculated.

The average values for the data obtained for water absorbency and for saline absorbency are compared in Table 3 for the polymeric networks of crosslinked polyaspartates of Examples 18–36. Also shown is the approximate ratio of the value for saline absorbency to water absorbency.

TABLE 3

WATER AND SALINE ABSORBENCY FOR CROSSLINKED POLYASPARTATES

| Polymeric Network | A Water Absorbency | B Saline Absorbency | Ratio B:A Absorbency |
|---|---|---|---|
| Ex. 18 | 10.5 | 7.4 | 0.7 |
| Ex. 19 | 5.6 | 4.6 | 0.8 |
| Ex. 20 | 8.9 | 5.8 | 0.7 |
| Ex. 21 | 5.5 | 4.0 | 0.7 |
| Ex. 22 | 16.9 | 9.3 | 0.6 |
| Ex. 23 | 8 | 5.3 | 0.7 |
| Ex. 24 | 3.7 | 3.7 | 1 |
| Ex. 25 | 13.1 | 7.9 | 0.6 |
| Ex. 26 | 14.6 | 6.2 | 0.4 |
| Ex. 27 | 8.3 | 5.8 | 0.7 |
| Ex. 28 | 8.6 | 8.3 | 1 |
| Ex. 29 | 6.9 | 5.6 | 0.8 |
| Ex. 30 | 28.3 | 13.5 | 0.5 |
| Ex. 31 | 5.7 | 4.4 | 0.8 |
| Ex. 32 | 71.3 | 21.4 | 0.3 |
| Ex. 33 | 93 | 23.4 | 0.3 |
| Ex. 34 | 4.2 | 4 | 1 |
| Ex. 35 | 3.1 | 2.9 | 1 |
| Ex. 36 | 5.2 | 5.3 | 1 |

As shown by the water absorbing data in Table 3, all of the polymeric networks absorbed at least about 3 times their weight to over 90 times their weight in water. As generally observed with all known water-swellable polymers, water absorbency decreased with increasing ionic strength of the solution. Thus, the overall absorbency generally is reduced in saline solution compared to that in water. Surprisingly, however, the water and saline absorbency of the polymeric networks of Examples 24, 28, 34, 35 and 36 were substantially similar as shown by the ratio of saline absorbency to water absorbency data.

By contrast, it was noted while practicing Method A, that the crosslinked polysuccinimides of Examples 1–17 did not swell in aqueous solutions, but did swell in the presence of polar organic solvents.

It is known from the art that for most polyacrylate based absorbents, the degree to which water absorbency is decreased by the presence of salts is quite large. Generally, the absorbency of 1% sodium chloride solution is less than about 20% of pure water absorbency. Thus, the water absorbing properties of the polymeric networks of the present invention are less sensitive to the presence of salts, as evidenced by the ratio of the saline absorbency to water absorbency in Table 3.

EXAMPLE 38

Synthesis of Polymeric Network of Polyaspartate by Method E

Polysuccinimide of about 50,000 $M_W$ (about 2000 g) was placed into a 50 liter round bottom flask. To this was added about 20 liters of sulfolane. The flask was purged with nitrogen, equipped with a Dean-Stark Trap and a condenser, an air motor with stir paddle and heating mantle. The mixture was heated with stirring agitation to a temperature of about 163° C. until the mixture formed a substantially homogeneous solution. The solution was then cooled to about 60° C. over a period of about 1.5 hours employing a copper coil heat exchanger with cold water flowing through the coil.

Triethyleneglycol diamine (about 214 g, neat) was added with stirring to the cooled solution. Heat was then applied to the resulting reaction medium until the reaction medium began to gel and the gel began to climb up the stirrer shaft.

The temperature of the reaction medium was about 72° C. at the gel point. Both stirring and heating were then discontinued and the resulting crosslinked polysuccinimide gel product was left undisturbed overnight.

The crosslinked polysuccinimide gel product was subsequently broken up into small particles employing a blender with water added (about 20 liters). The crosslinked polysuccinimide gel particles were then washed with an additional quantity of water (about 10 liters) and isolated by filtration. The filtered swollen crosslinked polysuccinimide gel product was then placed into a 50 liter round bottom flask and suspended in aqueous approximately 50% (v/v) isopropanol (about 30 liters) to deswell the gel. Aqueous 50% (w/w) sodium hydroxide (about 817 mL) was added to the suspension under stirring agitation. The alkaline suspension was stirred for about 2.5 hours to complete the hydrolysis of any remaining succinimide units to aspartate units and to deswell the polymeric network. The resulting deswollen super-absorbing polymeric network of polyaspartate (SPNP) was isolated by filtration.

The filtered SPNP was dehydrated by washing with isopropanol (about 10 liters) and the recovered SPNP was substantially dried by placing it in a forced-air convection oven for about 16 hours at about 100° C. A yield of about 2,700 g of substantially dry SPNP was recovered and collected.

The SPNP was evaluated for absorbency of electrolyte solution (synthetic urine) and for absorbency of water employing the following Blue Dextran Method.

Blue Dextran Method

Blue Dextran is a high molecular weight, water soluble polymer to which a blue colored dye is covalently attached and is available from Sigma Chemical Company in an average molecular weight of about 2,000,000. The method relies upon the exclusion of the Blue Dextran from super-absorbent materials during the absorption of water from a test solution.

The Blue Dextran Method utilizes stock solutions containing a concentration of about 0.3% (w/w) Blue Dextran (BD) in either deionized water or in an electrolyte solution, such as synthetic urine (SU). Synthetic urine was prepared by combining sodium chloride (10.09 g), calcium chloride dihydrate (0.3015 g), magnesium chloride (0.5938 g), and an aqueous solution of the nonionic surfactant, octoxynol-9, sold under the trademark TRITON®-X-100 by Union Carbide Corporation, (2.5 g of 1% solution) and diluting the combination to 1 liter with deionized water. A similar recipe can be found in U.S. Pat. No. 5,284,936 to Donachy et al. along with one description of the Blue Dextran Method, the relevant portions of which are incorporated herein by reference.

For assessing water absorbency, substantially dried SPNP was treated with Blue Dextran solution in the following manner. SPNP (about 100 mg) was stirred into about 20 grams of an aqueous Blue Dextran stock solution for about one hour. The suspension of resulting swollen SPNP gel was centrifuged for about 5 minutes at about 2,000 rpm. The optical absorbance of the supernatant at 617 nm was determined using a spectrophotometer. The optical absorbance of the Blue Dextran stock solution at 617 nm was also determined. For assessing electrolyte solution absorbency, the same procedure was followed, except that Blue Dextran stock solution containing synthetic urine (SU) was employed.

The specific absorbency of the polymer in water or in synthetic urine (SU) was then calculated by the following equation:

$$\text{Specific Absorbency (Water or SU)} = \left(\frac{\text{mass BD solution}}{\text{mass SPNP}}\right)\left(1 - \frac{\text{Absorbance BD solution}}{\text{Aborbance Supernatant}}\right)$$

In tabulating the data, it was noted whether the absorbency of Blue Dextran stock solution utilized was for water or for synthetic urine (SU).

The water and SU absorbency results in grams/gram polymer for the SPNP of Example 38 are shown in Table 4 below. Also shown is the approximate ratio of the value for SU absorbency to water absorbency.

Synthesis of Polymeric Networks of Polyaspartate by Method F

The following general procedure, herein referred to as Method F, was utilized for the synthesis of Examples 39–45. A mixture of about 19 grams polysuccinimide ($M_W$ about 50,000) and about 11 grams of orthophosphoric acid was placed in a beaker.

An amount of water equal to about 1 to about 10 times the weight of polysuccinimide was added to the beaker and the mixture was stirred. An aqueous solution of organic crosslinking diamine was then added to the mixture with stirring agitation employing a stirring blade driven by an overhead stir motor. Aqueous 18.94M sodium hydroxide (from 100 to 300 mole % based on succinimide units in the polysuccinimide) was gradually added over a period of time via a syringe pump. The reaction was exothermic, with temperatures reaching up to about 80° C., in some instances. After the addition of the sodium hydroxide, the resulting hydrolysis mixture was diluted with water (about 300 mL) and stirred for about 5 minutes and the resulting gel reaction product filtered.

The filtered gel reaction product was diluted to a volume in the range of about 400 mL to about 1000 mL with water. The pH of the diluted solution was adjusted to a value in the range of about 1 to about 5 with sulfuric acid. The gel product was isolated by filtering and then washed three times with water (about 400 mL). The washed gel was re-suspended in water (about 400 mL) and a sufficient amount of aqueous 18.94M sodium hydroxide was added to adjust the pH of the suspension to a pH value in the range of about 6 to about 12, preferably in the range of about 9 to about 10. To the resulting suspension of swollen SPNP gel was added a sufficient amount of methanol to deswell the gel (about 1 to about 10 volumes). The deswollen SPNP was recovered by decanting and drying the SPNP overnight in a vacuum oven set at about 70° C.

The substantially dried SPNP was ground to a substantially medium fine, sand-like powder. The ground SPNP was evaluated for absorbency of synthetic urine (i.e., electrolyte) and of water employing the Blue Dextran Method of Example 38.

EXAMPLES 39–45

Syntheses of Polymeric Networks of Polyaspartates by Method F

Examples 39–47 illustrate the super-absorbing characteristics of polymeric networks of crosslinked polyaspartates prepared by the general procedure of Method F, employing hexamethylenediamine (HMDA) as the crosslinking agent and the amounts and times as indicated below.

EXAMPLE 39

Aqueous 5.37M HMDA (0.0098 mole, 1.8 mL) was the crosslinking agent. Aqueous 18.94M sodium hydroxide (0.585 mole, about 30.9 mL) was added over a period of about 60 minutes to the mixture of polysuccinimide and phosphoric acid in about 60 g of water.

EXAMPLE 40

Aqueous 5.37M aqueous HMDA (0.0098 mole, 1.8 mL) was the crosslinking agent. Aqueous 18.94M sodium hydroxide (0.390 mole, about 20.6 mL) was added over a period of about 10 minutes to the mixture of polysuccinimide and phosphoric acid in about 60 g of water.

EXAMPLE 41

Aqueous 5.37M HMDA (0.0098 mole, 1.8 mL) was the crosslinking agent. Aqueous 18.94M sodium hydroxide (0.585 mole, about 30.9 mL) was added over a period of about 10 minutes to the mixture of polysuccinimide and phosphoric acid in about 60 g of water.

EXAMPLE 42

Aqueous 5.37M HMDA (0.015 mole, about 2.7 mL) was the crosslinking agent. Aqueous 18.94M sodium hydroxide (0.488 mole, about 25.8 mL) was added over a period of about 35 minutes to the mixture of polysuccinimide and phosphoric acid in about 105 g of water.

EXAMPLE 43

Aqueous HMDA (0.020 mole, about 3.6 mL) was the crosslinking agent. Aqueous 18.94M sodium hydroxide (0.585 mole, about 30.9 mL) was added over a period of about 10 minutes to the mixture of polysuccinimide and phosphoric acid in about 60 g of water.

EXAMPLE 44

Aqueous HMDA (0.020 mole, about 3.6 mL) was the crosslinking agent. Aqueous 18.94M sodium hydroxide (0.585 mmole, about 30.9 mL) was added over a period of about 60 minutes to the mixture of polysuccinimide and phosphoric acid in about 150 g of water.

EXAMPLE 45

Aqueous HMDA (0.020 mole, about 3.6 mL) was the crosslinking agent. Aqueous 18.94M sodium hydroxide (0.585 mmole, about 30.9 mL) was added over a period of about 60 minutes to the mixture of polysuccinimide and phosphoric acid in about 60 g of water.

The water and synthetic urine (SU) absorbency results for the SPNP of Examples 39–45 are shown in Table 4 below along with the approximate ratio of the value for SU absorbency to water absorbency.

EXAMPLES 46–47

Syntheses of Polymeric Networks of Polyaspartates by Alternative Variations of Method F Examples 46 and 47 each illustrates a variation of Method F by initially employing an undiluted polysuccinimide and acid mixture employing the amounts and steps as described below.

EXAMPLE 46

Aqueous 5.37 M aqueous HMDA (0.162 mole, about 30.2 mL) was combined with about 300 mL of water. The resulting solution was added to a mixture of polysuccinimide (about 158 g) and phosphoric acid (about 92 g). An aqueous 50% solution of sodium hydroxide (3.55 mole, about 284 g) was added dropwise to the mixture over a period of about 15 minutes. A substantially dry SPNP gel formed. The SPNP gel was then diluted with water (about 1,000 mL). The resulting swollen gel solution was then deswollen by adjusting the pH of the mixture with sulfuric acid (98%, about 150 g) to about pH 2. The acidified gel was filtered and then washed with water. The washed gel was then re-suspended in water (about 1,000 mL) and aqueous 18.94M sodium hydroxide was added to adjust the pH of the solution to about pH 12. The resulting gelatinous suspension was deswollen by the addition of isopropanol (about 2,000 mL) and then the supernatant was decanted. The decanted recovered SPNP gel was dehydrated with methanol (about 3,000 mL) and then further dried overnight in a vacuum oven set at a temperature of about 70° C.

EXAMPLE 47

Ice (about 1250 g) and aqueous 5.37M HMDA (0.163 mole, about 30.4 mL) were combined and continuously stirred. A mixture of polysuccinimide (about 315 g) and phosphoric acid (about 185 g) was added followed by addition of sodium hydroxide (8.13 mole, about 325 g) pellets. The resulting reaction medium was stirred for a period of about 90 minutes after the sodium hydroxide addition. Within about 15 minutes a gel formed. The gel was diluted with water (about 1,000 mL) and then deswollen by adjusting the pH of the mixture with sulfuric acid (98%, about 150 g) to about pH 2. The resulting SPNP gel was filtered and was washed with water (about 3,000 mL). The washed SPNP was then re-suspended in water (about 1,000 mL) and aqueous 18.94M sodium hydroxide (about 350 g) was added to adjust the pH of the suspension to about pH 12. The suspended gel was deswollen by the addition of methanol (about 3,000 mL) and then the supernatant was decanted. The deswollen SPNP gel was dehydrated with methanol (about 3,000 mL) and further dried overnight in a forced air convection oven set at about 70° C.

The water and SU absorbency results for the SPNP of Examples 46 and 47, determined by the Blue Dextran Method, are shown in Table 4 below along with the approximate ratio of the value for SU absorbency to water absorbency.

TABLE 4

WATER AND SYNTHETIC URINE (SU) ABSORBENCY (GRAMS/GRAM POLYMER) FOR CROSSLINKED POLYASPARTATES

| Polymeric Network | A Water Absorbency | B SU Absorbency | Ratio B:A Absorbency |
|---|---|---|---|
| Ex. 38 | 78.5 | 28.8 | 0.4 |
| Ex. 39 | 161.0 | 19.2 | 0.1 |
| Ex. 40 | 138.0 | 20.8 | 0.2 |
| Ex. 41 | 170.0 | 23.7 | 0.1 |
| Ex. 42 | 146.0 | 28.0 | 0.2 |
| Ex. 43 | 41.0 | 28.1 | 0.7 |
| Ex. 44 | 269.0 | 30.0 | 0.1 |
| Ex. 45 | 78.2 | 33.3 | 0.4 |
| Ex. 46 | 29.5 | 9.8 | 0.3 |
| Ex. 47 | 155.0 | 20.0 | 0.1 |

As shown by the water absorbency data in Table 4, except for the SPNP of Ex. 46, all of the polymeric networks absorbed at least 41 times their weight to over 260 times their weight of water. As generally observed with all known water-swellable polymers, water absorbency decreased with increasing ionic strength of the solution. Thus, the overall absorbency generally was reduced in the synthetic urine (electrolyte) solution compared to that in water as illustrated by the ratio of SU absorbency to water absorbency. However, again except for the SPNP of Ex. 46, all the polymeric networks absorbed at least 19 to over about 30 times their weight of synthetic urine (SU).

The SPNP of Example 46 for reasons not fully understood was less absorbent of water and synthetic urine compared to the SPNP of Examples 38–45 and 47, but still absorbed at least about 29 times its own weight of water and at least about 9 times its own weight of SU.

What is claimed is:

1. A method of producing polymeric networks of crosslinked polyaspartate comprising the steps of sequentially:
   (a) reacting a polysuccinimide with an effective crosslinking amount of a diamine crosslinking agent in a reaction medium and at a temperature sufficient to form a gelled crosslinked polysuccinimide product;
   (b) base hydrolyzing the gelled crosslinked polysuccinimide product to a gelled polymeric network of polyaspartate;
   (c) isolating the gelled polymeric network of polyaspartate;
   (d) contacting the gelled polymeric network of polyaspartate, at a pH in the range of about 6 to about 12, with at least one liquid, monohydric, aliphatic alcohol; and
   (e) recovering a deswelled polymeric network of polyaspartate.

2. The method of claim 1 wherein the reaction medium in step (a) includes a liquid selected from the group consisting of water, water-miscible polar aprotic solvent, and a mixture thereof.

3. The method of claim 1 wherein the reaction medium in step (a) is at a temperature in the range of about 25° C. to about 80° C. and is maintained in said temperature range until the gelled crosslinked polysuccinimide product forms.

4. The method of claim 1 wherein step (d) is performed concurrently with step (b).

5. The method of claim 1 wherein the gelled crosslinked polymeric network of polyaspartate is isolated by washing with a liquid selected from the group consisting of water, alcohol and a mixture thereof.

6. The method of claim 1 wherein the polymeric network of polyaspartate is recovered in step (e) by filtering.

7. The method of claim 1 wherein the reaction medium includes a mineral acid.

8. The method of claim 1 wherein the isolating step comprises acidifying the gelled polymeric network of polyaspartate to a pH value in the range of about 1 to about 5, washing the so-acidified product with water, and suspending the so-washed product in water.

9. The method of claim 1 wherein the polysuccinimide has a weight average molecular weight in the range of about 500 to greater than about 150,000.

10. The method of claim 1 wherein the amount of diamine crosslinking agent based on moles of diamine per mole of succinimide monomer units in the polysuccinimide is present in an amount of about 0.1 to about 50 mole percent.

11. A composition of matter comprising a random copolymer of crosslinked polyaspartate produced by the method of claim 1 and capable of absorbing water in an amount in the range of at least 25 times to over about 260 times its dry weight.

12. A composition of matter comprising a polymeric network produced by the method of claim 1 and capable of absorbing an electrolyte solution in an amount in the range of at least 5 times to over 40 times its dry weight.

13. A method of producing a polymeric network of polyaspartate comprising the steps of:
   (a) preparing a reaction medium by combining an aqueous solution of polysuccinimide and an organic base containing at least two primary amine groups;
   (b) adding sufficient base to the reaction medium to crosslink the polysuccinimide and hydrolyze remaining succinimide units in the polymer so as to form a gelled polymeric network of polyaspartate;
   (c) isolating the gelled polymeric network of polyaspartate by sequentially (i) filtering, (ii) suspending the filtered product in water acidified to a pH in the range of 1 to about 5, (iii) washing the filtered product with water, (iv) suspending the washed product in water containing sufficient alkali to form a gelatinous suspension of polymeric network of polyaspartate;
   (d) adding to the gelatinous suspension a liquid, monohydric, aliphatic alcohol; and
   (e) recovering a deswelled polymeric network of polyaspartate.

14. The method of claim 13 wherein the reaction medium includes a mineral acid.

15. The method of claim 13 wherein the pH of the gelatinous suspension is about 12.

16. The method of claim 13 wherein step e) includes substantially drying the polymeric network of polyaspartate.

17. A composition of matter which includes a polymeric network produced by the method of claim 13 and comprises a random copolymer of crosslinked polyaspartate capable of absorbing water in an amount in the range of at least 25 times to over 260 times its dry weight.

18. A composition of matter which includes a polymeric network produced by the method of claim 13 and comprises a random copolymer of crosslinked polyaspartate capable of absorbing an electrolyte solution in an amount in the range of at least 5 times to over 40 times its dry weight.

19. The composition of matter of claim 18 wherein the electrolyte solution is a body fluid.

* * * * *